United States Patent [19]

Kleiner et al.

[11] Patent Number: 5,571,779
[45] Date of Patent: Nov. 5, 1996

[54] METHOD OF LUBRICATION USING PERFLUOROALKYL TERMINATED URETHANES

[76] Inventors: Eduard K. Kleiner, 29 Hemlock Hill Rd., Pound Ridge, N.Y. 10576; Athanasios Karydas, 400 E. 71st St., New York, N.Y. 10021

[21] Appl. No.: 558,905

[22] Filed: Nov. 15, 1995

Related U.S. Application Data

[62] Division of Ser. No. 972,825, Nov. 9, 1992, Pat. No. 5,502,225.

[51] Int. Cl.$^6$ ...................... C10M 105/08; C10M 105/54
[52] U.S. Cl. ............................................ 508/153; 508/551
[58] Field of Search ........................ 252/51, 47.5, 51.5 R, 252/51.5 A, 54.6, 58; C10M 105/54, 105/08

[56] References Cited

U.S. PATENT DOCUMENTS 5,502,225  3/1996  Kleiner et al. ............................ 554/42

*Primary Examiner*—Prince Willis, Jr.
*Assistant Examiner*—Cephia D. Toomer
*Attorney, Agent, or Firm*—Mathews, Woodbridge & Collins

[57] ABSTRACT

This invention relates to perfluoroalkyl group terminated urethanes, thiourethanes and ureas of the general formula $$(R-X-CONH)_m A$$

where m is 1, 2 or 3, R is $R_f$—E and optionally $R_1$ with the proviso that at least one R is $R_f$—E, $R_f$ is a perfluoroalkyl group, $R_1$ is a hydrocarbon group, E is a divalent linking group, X is —O—, —S—, —$NR_2$— and $R_2$ is H or lower alkyl and A is $R_f E$ or $R_1$ if m is 1 and a divalent or trivalent linking group if m is 2 or 3 respectively. Compounds of this general formula are useful as solid lubricants or as additives for waxes and resins providing lubricating properties.

25 Claims, No Drawings

METHOD OF LUBRICATION USING PERFLUOROALKYL TERMINATED URETHANES

This is a divisional of application Ser. No. 07/972,825 filed on Nov. 9, 1992, now U.S. Pat. No. 5,502,225.

BACKGROUND OF INVENTION

This invention relates to compounds useful as lubricants per se or as wax and resin additives providing excellent lubricating or low friction properties. The solid lubricants of this invention can be brittle and hard solids or can have the physical properties of waxes. Waxes are defined as substances which are plastic solids at ambient temperature and, on being subjected to moderately elevated temperatures, become low viscosity liquids. Waxes having low frictonial properties are of special importance as ski waxes. Some of the compounds described in this invention are not having the solid state properties of waxes but are important as additives to waxes and resins and especially to hydrocarbon waxes providing low friction properties.

It is well known that different types of ski waxes are being used to achieve the smoothest gliding and therefore highest speed under different snow and weather conditions. In ski racing, for instance, a difference of one-hundredth of a second can mean winning or losing a race; and therefore, the selection of the right type of ski wax for a given snow and weather condition is most important.

It is also well known that most ski waxes used today are hydrocarbon waxes having different hardness and melting points. Hydrocarbon waxes used as ski waxes are paraffin waxes consisting principally of normal alkanes or synthetic waxes such as low molecular weight polyethylene having wax-like properties.

Hydrocarbon ski waxes with melting points below 50° C. are too soft and not sufficiently abrasion resistant, while hydrocarbon waxes with melting points much above 100° C. would damage ski bases made of extruded or sintered polyethylene, when applied as a hot melt, since polyethylene has a melting point of approximately 120° C.

Depending on the type of snow, snow temperature and snow moisture, as well as air temperature and air humidity, the following type of ski waxes are recommended to achieve the highest speed and best control:

The softest and lowest melting hydrocarbon waxes are recommended for snow temperatures of −3° to −4° C. and above.

Medium hard, higher melting hydrocarbon waxes are recommended for snow temperatures in the range of −3° to −10° C.

The hardest and highest melting hydrocarbon waxes are recommended for snow temperatures of about −10° C. and below. Commercial hydrocarbon based ski waxes were found to have melting points as low as 55° C. and as high as 95° C.

By mixing ski waxes of the above type in different ratios, ski waxes can be tuned to specific conditions present on a racing parcour in order to take other variables besides snow temperature into account.

In addition to snow temperature, the following will influence how much softer or harder the optimum hydrocarbon ski wax has to be:

For softer, less abrasive snow and snow with high humidity content, softer hydrocarbon waxes give better results.

For harder, more abrasive snow and snow with low humidity content, harder and more abrasion resistant hydrocarbon waxes give better results.

If skis are in contact with the snow for seconds or minutes such as in ski-jumping and alpine ski racing, somewhat softer and less abrasion resistant waxes can be used, while for cross country racing lasting hours, harder and more abrasion resistant hydrocarbon waxes are preferred.

While hydrocarbon waxes with melting points between 50° and 100° C. offer the ski racer a lot of flexibility to achieve the highest speed under many different conditions, it has been found that certain perfluorocarbons are superior ski waxes if used under certain snow conditions.

U.S. Pat. No. 4,724,093 describes solid lubricants consisting of solid perfluorocarbons with linear or substantially linear carbon atom chain, containing from 10 to 20 carbon atoms and having surface tensions ranging from 13 to 15 dyne/cm. Perfluorocarbons as described in U.S. Pat. 4,724, 093 have melting points which range from 36° C. for $C_{10}F_{22}$, to 70° C. for $C_{13}F_{28}$ and 108°–110° C. for $C_{16}F_{34}$. Fluorocarbon blends used commercially have melting points as high as 108° C.

Because of the low critical surface energy of 13 to 15 dyne/cm, fluorocarbons of the above type have superior water and oil repellent properties. The superior water repellency of these perfluorocarbons make them superior to hydrocarbon waxes on snow having a temperature close to or at the freezing point and on very wet snow. Skis treated with the more hydrophobic (water repellent) perfluorocarbons will glide easier on the water layer generated between the ski base and the snow. The speed retarding suction effect caused by too heavy a layer of water between the ski base and the snow is reduced and speed, therefore, increased. It is also claimed that the oil repellent properties of the perfluorocarbons will reduce the contamination by oily soil, which reduces speed and is of special importance in cross country racing.

While the costly perfluorocarbons have shown their superiority over hydrocarbon waxes on wet snow, and are commercially used in ski racing, they have also been shown to have limitations if compared with the flexibility, safety and low cost that the hydrocarbon waxes offer.

Hydrocarbon waxes are miscible with each other and, therefore, give the ski racer the possibility to prepare the right wax blend right before a race having the ideal hardness by simply melting and mixing different hydrocarbon ski waxes.

Since perfluorocarbons are not miscible with hydrocarbon waxes, this on-site adjustment opportunity to specific snow conditions is not possible.

While perfluorocarbon waxes used commercially are very hard and high melting and should therefore have a better abrasion resistance than softer hydrocarbon waxes recommended for wet snow, they have a disadvantage which limits their durability; perfluorocarbon waxes in contrast to hydrocarbon waxes are not compatible with polyethylene ski bases. Therefore, polyethylene ski bases cannot be saturated with perfluorocarbon waxes, which would provide the increased durability especially important in cross country racing.

While perfluorocarbon waxes are inert and non-toxic products, they can represent a serious health hazard, if not properly handled. Perfluorocarbons used commercially as ski waxes have a melting range of up to 108° C. and have, therefore, to be heated by heating irons having a recommended minimum temperature of 150° C. Because perfluorocarbons have no hydrogen bonding, they have a great tendency to sublime at elevated temperature. The inhalation of airborne perfluorocarbon particles and especially decomposition products formed during the application of perfluorocarbon waxes can represent a serious risk of pulmonary edema as documented by K. P. Lee and W. C. Seidel (Haskell Lab. Toxicol. Ind. Med., DuPont Co., Newark, Del. 19714 U.S.A.).

European Patent Application 0 421 303 A2 describes lubricants for skis, which comprise a fluorine compound containing a polyfluoroalkyl group and having a melting point of at most 100° C., wherein the fluorine compound is at least one member selected from the group consisting of an alcohol containing a polyfluoroalkyl group, an ester containing a polyfluoroalkyl group, and a polyfluoroalkyl ester copolymer of (meth)acrylic acid. This application claims that perfluorocarbons as claimed in U.S. Pat. No. 4,724,093 having the formula $C_{2n}F_{2n+2}$ are having drawbacks as ski lubricants because of poor adhesion to the ski bases, possible degradation of the polyethylene ski base due to the high temperature required for their application, and, finally, poor abrasion resistance.

Fluoroalcohols and fluoroesters claimed in European Patent 0 421 303 have melting points of 50° C. or less which makes them unsuitable for use as ski waxes per se, not having the desired melting point range of 50° to 100° C. In addition, the recommended fluoroalcohols are not miscible with hydrocarbon waxes.

The lubricants of this invention, be they hard solids, waxes or wax and resin additives are structurally different from prior art lubricants providing low friction properties for applications such as ski waxes or ski wax additives. Depending on the structure, they are miscible with hydrocarbon ski waxes.

In addition, the compounds of this invention offer other advantages over prior art ski waxes. The urethane, thiourethane and urea linkage groups provide very strong hydrogen bonding, which reduces sublimation and the potential health problems associated with perfluorocarbons when applied to skis by the hot melt process.

The lubricants of this invention, when used as ski waxes, can be applied using conventional wax application methods, such as the hot melt method, applying the wax with a hot iron to the ski base, or by spraying a solution of wax in a solvent onto the ski base, or by impregnating paper, nonwovens and other substrates with the ski wax and transferring the ski wax to the ski base with a hot iron.

Lubricants of this invention, in addition to being miscible with hydrocarbon waxes, can also be blended or milled with perfluorocarbon waxes and it is understood that conventional additives used in ski waxes to improve abrasion resistance, hardness, low friction properties, etc., can also be added to lubricants of this invention. Such additives can be powdered polyethylene, polytetrafluoroethylene, graphite, fluorinated graphite, and other inorganic or organic additives.

DETAILED DISCLOSURE

The compounds of this invention, useful as solid lubricants and additives for waxes and resins providing lubricating properties are perfluoroalkyl group ($R_f$-group) containing urethanes (also called carbamates), thiourethanes (also called thiocarbamates), and ureas, referred to as "$R_f$-urethanes" and have the general formula $$(R-X-CONH)_m A \quad (I)$$

wherein m is 1, 2 or 3

R is $R_f$—E and optionally $R_1$ with the proviso that at least one R is $R_f$—E; $R_f$ is independently a straight or branched perfluoroalkyl group of 6 to 20 carbon atoms or said perfluoroalkyl substituted by perfluoroalkoxy of 2 to 6 carbon atoms; E is independently a divalent linkage group and can be a straight or branched alkylene group of 1 to 16 carbon atoms or said alkylene group interrupted by one to three groups selected from the group consisting of —$NR_2$—, —O—, —S—, —$SO_2$—, —COO—, —OOC—, —$CONR_2$—, —$NR_2CO$—, —$SO_2NR_2$—, —$NR_2SO_2$— or terminated at the $R_f$-end with —$CONR_2$— or —$SO_2NR_2$—, where $R_f$ is attached to the carbon or sulfur atom and wherein $R_2$ is independently hydrogen or alkyl of 1 to 6 carbon atoms; $R_1$ is straight or branched alkyl or aralkyl, including lower alkyl substituted aralkyl with up to 36 carbon atoms, X is —O—, —S—, or —$NR_2$—, A is $A_1$, if m is 1, $A_2$ if m is 2 and $A_3$ if m is 3 and $A_1$ is $R_1$ or $R_f$—E—, $A_2$ is a divalent aliphatic, cycloaliphatic or aromatic radical of an aliphatic, cycloaliphatic or aromatic diisocyanate with up to 36 carbon atoms, $A_3$ is a trivalent aliphatic, cycloaliphatic or aromatic radical of an aliphatic, cycloaliphatic or aromatic triisocyanate with up to 36 carbon atoms.

It is understood that the $R_f$ group usually represents a mixture of perfluoroalkyl moieties. When the $R_f$ group is identified as having a certain number of carbon atoms, said $R_f$ group also usually concomitantly contains a small fraction of perfluoroalkyl groups with a lower number of carbon atoms and a small fraction of perfluoroalkyl groups with a higher number of carbon atoms.

Preferred compounds are those where m is 1, 2 or 3,

R is $R_f$—E if m is 1, one R is $R_f$—E and one R is $R_1$ if m is 2, one or two R groups are $R_f$—E and two or one R groups are $R_1$ respectively, $R_f$ is a straight or branched perfluoroalkyl group of 6 to 20 carbon atoms, E is alkylene of 2 to 12 carbon atoms, —$CONR_2CH_2CH_2$—, —$SO_2NR_2CH_2CH_2$—, —$CH_2CH_2OCH_2CH_2$— and —$CH_2CH_2SCH_2CH_2CH_2$—, wherein $R_2$ is —H, —$CH_3$ or —$CH_2CH_3$, $R_1$ is straight or branched alkyl with 8 to 36 carbon atoms, X is —O— or —S—, $A_1$ is $R_1$, $A_2$ is a divalent aliphatic, cycloaliphatic or aromatic radical of an aliphatic, cycloaliphatic or aromatic diisocyanate with 6 to 36 carbon atoms.

Most preferred compounds are those where m is 1 or 2,

R is $R_f$—E if m is 1, one R is $R_f$—E and the other R is $R_1$ if m is 2, $R_f$ is straight perfluoroalkyl group of 8 to 20 carbon atoms, E is ethylene, $R_1$ is straight or branched alkyl of 12 to 36 carbon atoms, X is —O— or —S—, $A_1$ is $R_1$ and $A_2$ is a divalent aliphatic hydrocarbon radical of an aliphatic diisocyanate with 6 to 18 carbon atoms.

Useful aliphatic and cycloaliphatic diisocyanates of formula $A_2(NCO)_2$, include:

1,2-ethane diisocyanate, 1,3-propane diisocyanate, 1,4-butane diisocyanate, 2-chloropropane-1,3-diisocyanate, pentamethylene diisocyanate, propylene-1,2-diisocyanate, 1,10-decane diisocyanate, 1,12-dodecane diisocyanate, 1,16-hexadecane diisocyanate and other aliphatic diisocyanates such as 1,3-cyclohexane diisocyanate, 1,4-cyclohexane diisocyanate, 4,4'-methylene bis(cyclohexyl isocyanate), 2,2,4- and 2,4,4,-trimethylhexamethylene diisocyanate (TMDI), dimer acid derived diisocyanate (DDI) obtained from dimerized fatty acids, such as linoleic acid, 4,4'-dicyclohexylmethane diisocyanate (hydrogenated MDI), isophorone diisocyanate, 3-isocyanatomethyl-3,5,5-trimethylcyclohexyl diisocyanate, lysine methyl ester diisocyanate (LDIM), bis(2-isocyanatoethyl) fumarate (FDI), bis(2-isocyanatoethyl) carbonate, m-tetramethylxylylene diisocyanate (TMXDI).

Useful aromatic diisocyanates of formula $A_2(NCO)_2$ include:

Tolylene diisocyanate (TDI) (all isomers), 4,4'-diphenylmethane diisocyanate (MDI), tolidine diisocyanate, dianisidine diisocyanate, m-xylylene diisocyanate, p-phenylene diisocyanate, m-phenylene diisocyanate, 1-chloro-2,4-phenyl diisocyanate, 3,3'-dimethyl- 4,4'-bisphenylene diisocyanate, 4,4'-bis(2-methylisocyanatophenyl)methane, 4,4'-bisphenylene diisocyanate, 4,4'-bis(2-methoxyisocyanatophenyl)methane, 1-nitrophenyl- 3,5-diisocyanate, 4,4'-diisocyanatodiphenyl ether, 3,3'-dichloro-4,4'-diisocyanatodiphenyl ether, 3,3'-dichloro, 4,4,'-diisocyanatodiphenyl-methane, 4,4'-diisocyanatodibenzyl, 3,3'-dimethoxy-4,4'-diisocyanatodiphenyl, 2,2'-dimethyl-4,4'-diisocyanatodiphenyl, 2,2'-dichloro- 5,5'-dimethoxy-4,4'-diisocyanatodiphenyl, 3,3'dichloro-4,4'-diisocyanatodiphenyl, 1,2-naphthalenediisocyanate, 4-chloro-1,2-naphthalenediisocyanate, 4-methyl-1,2-napthalene diisocyanate, 1,5-naphthalene diisocyanate, 1,6-naphthalene diisocyanate, 1,7-naphthalene diisocyanate, 1,8-naphthalene diisocyanate, 4-chloro-1,8-naphthalene diisocyanate, 2,3-naphthalene diisocyanate, 2,7-naphthalene diisocyanate, 1,8-dinitro-2,7-naphthalene diisocyanate, 1-methyl-2,3-naphthalene diisocyanate, 1-methyl-5,7-naphthalene diisocyanate, 6-methyl-1,3-naphthalene diisocyanate, 7-methyl-1,3-naphthalene diisocyanate.

Useful aliphatic triisocyanates of formula $A_3(NCO)_3$ include isocyanates which are readily obtained by the reaction of three moles of one or more diisocyanates with one mole of water according to the following equation:

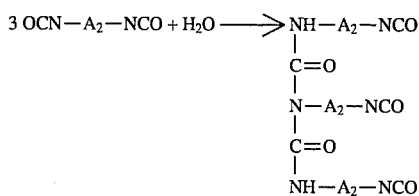

where $A_2$ is one or more of the radicals previously described.

Other useful aliphatic triisocyanates include isophorone diisocyanate trimer and hexamethylene diisocyanate trimer.

Useful aromatic triisocyanates of formula $A_3(NCO)_3$ include:

benzene-1,2,4-triisocyanate, benzene-1,3,5-triisocyanate, benzene-1,2,3-triisocyanate, toluene 2,4,6-triisocyanate, and toluene 2,3,4-triisocyanate.

$R_f$-urethanes of general formula (I) can be subdivided into Groups A and B:

Group A, wherein all R groups are $R_f$—E— and $A_1$ is $R_f$—E:

$$R_f-E-X-CONH-E-R_f \qquad (II)$$

$$(R_f-E-X-CONH)_2-A_2 \qquad (III)$$

$$(R_f-E-X-CONH)_3-A_3 \qquad (IV)$$

Group B, wherein R is $R_f$—E— and $R_1$:

$$R_f-E-X-CONH-R_1 \qquad (V)$$

$$R_f-E-X-CONH-A_2-NHCO-X-R_1 \qquad (VI)$$

$$(R_f-E-X-CONH)_2-A_3-NHCO-X-R_1 \qquad (VII)$$

$$R_f-E-X-CONH-A_3-(NHCO-X-R_1)_2 \qquad (VIII)$$

A number of compounds belonging to Group A or Group B have been described in the patent literature useful for enduses other than as lubricants and wax and resin additives providing lubricating properties. For example, the following compounds of Group A and B are recommended in the patent literature as oil and water repellent finishes for textiles, fibers and carpets:

| | |
|---|---|
| DE 3514373 and JP 59094621 | 2,4-$(R_fCH_2CH_2OCONH)_2$-$C_6H_3$—$CH_3$ |
| JP 3249236 | $C_8F_{17}CH_2CH_2OCONH(CH_2)_6NHCOOC_2H_5$ |
| JP 2209984 | $R_fC_nH_{2n}OCONH$—R—NHCOOR, ($R_1$ = alkyl with 1 to 4 carbons) |
| JP 5909575 | $R_fCH_2CH_2OCONH$—$C_6H_3(CH_3)$—$NHCOOCH_3$ |
| US 4835300 | Adduct of $(CF_3)_2CH(CH_2)_6CH_2CH_2OH$ and p,p',p"-triphenyl methane triisocyanate |
| JP 59031751 | $R_fCH_2CH_2OCONH$—$C_6H_4$—CH—$(C_6H_4$—NHCOOMe$)_2$ |
| JP 58126369 and JP 58109680 | $R_fCH_2CH_2OCONH$—$C_6H_3(CH_3)NHCOOCH_3$ |
| JP 54074000 | $R_fCH_2CH_2OCONH$—Z—NHCOO-Alkyl, with 1 to 4 carbons |
| JP 53112855 | $R_fCH_2CH_2OCONH$—$C_6H_3(CH_3)NHCOOC_6H_5$ |
| DE 2821495 | $(C_8F_{17}CH_2CH_2OCONHCH_2CH_2CH_2)_2$— |

DE 2821495 describes the above diurethane useful as a dirt release additive if added to lacquers.

Compounds of Group A and B or blends of compounds of Group A and B are of interest primarily as ski waxes per se if they have melting points in the 50° to 100° C. range. Compounds of Group B, wherein $R_1$ is alkyl, aralkyl, and lower alkyl substituted aralkyl with 8 to 36 carbon atoms are especially useful as miscible additives to hydrocarbon ski waxes improving the lubricating properties of the hydrocarbon ski waxes. In addition, these Group B compounds can be absorbed by polyethylene ski bases and have superior water repellent properties of importance when used at snow temperatures near the melting point and on very moist snow or when air humidity is very high.

The $R_f$-urethanes, thiourethanes and ureas of this invention are obtained from isocyanates of the type $A_1NCO$, $A_2(NCO)_2$ and $A_3(NCO)_3$ and $R_f$-alcohols, $R_f$-mercaptans and $R_f$-amines of the type $R_f$—E—OH, $R_f$—E—SH and $R_f$—E—$NHR_2$ and hydrocarbon alcohols, mercaptans and amines of the type $R_1$—OH, $R_1$—SH, $R_1$—$NH_2$, and $(R_1)_2NH$.

Monoisocyanates of the type $A_1NCO$ include:

Methyl isocyanate, ethyl isocyanate, propyl isocyanate, butyl isocyanate, t-butyl isocyanate, hexyl isocyanate, octyl isocyanate, dodecyl isocyanate, hexadecylisocyanate, octadecyl isocyanate, and mixtures thereof, as well as cyclohexyl isocyanate, trans-2-phenylcyclopropyl isocyanate, m-tolyl isocyanate, p-tolyl isocyanate, 2,5-dimethylphenyl isocyanate, o-ethoxyphenyl isocyanate, p-ethoxyphenyl isocyanate, o-methoxyphenyl isocyanate, m-methoxyphenyl isocyanate, p-methoxyphenyl isocyanate, l-naphthyl isocyanate, o-tolyl isocyanate.

$R_f$-group terminated monoisocyanates of the type $A_1NCO$ are also documented in the prior art and include $R_fCH_2CH_2NCO$ as described in J. Fluorine Chem. 1992, 56(1), 85–92.

Useful aliphatic and aromatic di- and triisocyanates of the type $A_2(NCO)_2$ and $A_3(NCO)_3$ have been described previously.

$R_f$-alcohols, $R_f$-mercaptans and $R_f$-amines useful herein are well documented in the prior art.

$R_f$-alcohols of the type $R_f$—E—OH useful for purposes of this invention are taught in U.S. Pat. Nos. 3,655,732, 3,282,905, 2,642,416, 3,102,103, 4,302,366, 4,266,080, 4,310,698 and others.

Typical alcohols which are included within the context of this invention include:

$C_7F_{13}CH_2OH$
$C_6F_{13}CH_2CH_2OH$
$C_8F_{17}CH_2CH_2OH$
$C_{10}F_{21}CH_2CH_2OH$
$C_{12}F_{25}CH_2CH_2OH$
$C_{14}F_{29}CH_2CH_2OH$
$C_{16}F_{23}CH_2CH_2OH$
$C_{18}F_{37}CH_2CH_2OH$
$C_8F_{17}CH_2CH_2SCH_2CH_2CH_2OH$
$C_6F_{13}CH_2CH_2CH_2OCH_2CH_2OH$
$C_{10}F_{21}CH_2OH$
$C_8F_{17}CH_2CH_2S(CH_2)_{11}OH$
$C_8F_{17}CH_2CH_2SO_2N(C_2H_5)CH_2CH_2OH$
$C_6F_{13}CH_2CH_2N(CH_3)CH_2CH_2OH$
$C_8F_{17}CH_2CH_2SO_2CH_2CH_2OH$
$C_7F_{15}SO_2N(C_2H_5)CH_2CH_2OH$
$C_7F_{15}CON(C_2H_5)CH_2CH_2OH$ $R_f$-mercaptans of the type $R_f$—E—SH are also well documented in the prior art. For example mercaptans of the formula $R_f$—E—SH have been described in a number of U.S. patents including U.S. Pat. Nos. 2,894,991; 2,961,470; 2,965,677; 3,088,849; 3,172,190; 3,544,663 and 3,655,732.

Thus, U.S. Pat. No. 3,655,732 discloses mercaptans of formula $R_f$—$R_1$—SH where $R_1$ is alkylene of 1 to 16 carbon atoms and $R_f$ is perfluoroalkyl.

U.S. Pat. No. 3,655,732 further discloses compounds of formula $R_f$—$R_1$—X—$R_1$—SH where the $R_1$'s are independently alkylene of 1 to 16 carbon atoms; $R_f$ is perfluoroalkyl of 4 through 14 carbon atoms and X is —S— or —$NR_4$— where $R_4$ is hydrogen or alkyl of 1 to 4 carbon atoms.

U.S. Pat. No. 3,544,633 teaches that the mercaptan $R_fCH_2CH_2SH$ where $R_f$ is perfluoroalkyl of 5 to 13 carbon atoms, can be prepared by reacting the perfluoroalkyl alkylene iodide with thiourea or by adding $H_2S$ to a perfluoroalkyl substituted ethylene ($R_f$—CH=$CH_2$). The reaction of the iodide $R_fCH_2CH_2I$ with thiourea followed by hydrolysis to obtain the mercaptan $R_fCH_2CH_2SH$ is the preferred synthetic route.

Typical mercaptans which are included within the context of this invention are:
$C_6F_{13}CH_2CH_2SH$
$C_8F_{17}CH_2CH_2SH$
$C_{10}F_{21}CH_2CH_2SH$
$C_{12}F_{25}CH_2CH_2SH$
$C_{14}F_{29}CH_2CH_2SH$
$C_{18}F_{37}CH_2CH_2SH$
$C_8F_{17}CH_2CH_2OCH_2CH_2CH_2SH$
$C_6F_{13}CH_2CH_2N(CH_3)CH_2CH_2CH_2SH$
$C_8F_{17}CH_2CH_2SCH_2CH_2CH_2SH$
$C_8F_{17}CH_2CH_2SO_2NHCH_2CH_2CH_2SH$ The preparation of perfluoroalkylamines of formula $R_f$—E—$NHR_2$ are taught in U.S. Pat. Nos. 3,369,064; 3,663,604; 3,808,251; 3,838,165; 4,059,629; German DE Nos. 1,961,552; 2,357,780; 2,504,514 and Japan Nos. 57/190008 and 52/14767.

Typical $R_f$-amines include:
$C_8F_{17}CH_2CH_2NH_2$
$C_6F_{13}CH_2CH_2CH_2CH_2NH_2$
$C_8F_{17}CH_2CH_2NH_2$
$R_fSO_2NR(CH_2)_nNR(CH_2)_3NH_2$
$R_fCONH(CH_2)_nNH_2$ Hydrocarbon alcohols, mercaptans and amines of the type $R_1$—OH, $R_1$—SH, $R_1$—$NH_2$, and $(R_1)_2NH$ are well known commodity chemicals, wherein $R_1$ is straight or branched alkyl or aralkyl, with 1 to 36 carbon atoms.

The synthesis of $R_f$-urethanes, $R_f$-thiourethanes and $R_f$-ureas is analogous to the synthesis of urethanes, thiourethanes and ureas as described in Houben-Weyl, Methoden der Organischen Chemie, Vol. 8, p. 119–137, 149–158, (1952), Vol. 14/2, p. 57–98, 165–171 (1963) and Vol. E20, p. 1561–1594, 1721–1752 (1987), Georg Thieme Verlag, Stuttgart.

The reaction between the isocyanates and alcohols, mercaptans or amines can be carried out in bulk, i.e., without solvent, or in the presence of organic solvents which do not contain active hydrogens. Solvents in which the reaction can be carried out include ketones, such as acetone, methylethyl ketone and methylisobutyl ketone; esters such as ethyl acetate, butyl acetate, 2-ethylhexyl acetate. It is also possible to employ ethers, including di-n-propyl ether, di-butyl ether, tetrahydrofuran and the diether of polyalkylene oxides. In addition, chlorinated solvents such as dichloroethyl ether, ethylene dichloride, perchloroethylene and carbon tetrachloride can be used. In all cases, the solvents should be anhydrous to avoid urea formation.

The reaction can, if desired, be catalyzed and those catalysts conventionally employed in the urethane art are useful herein. Useful catalysts fall principally in two groups.

(a) amino compounds:

triethylamine and other trialkylamines
1,4-diaza-2,2,2-bicyclooctane
N-(lower alkyl) morpholines
N, N, N', N'-tetramethylethylenediamine
N, N, N', N'-tetramethyl-1,3-butanediamine
N, N'-substituted piperazines
benzyltrimethylammonium chloride (b) organometallic and inorganic compounds:
cobalt naphthenate
stannous octoate
stannous oleate
dimethyltin dichloride
di-n-butyltin dilaurlmercaptide
tetra-n-butyltin
trimethyltin hydroxide
di-n-butyltin dilaurate
stannous chloride Such catalysts may be used singly or in combination with each other. Beneficial synergistic catalysts may occur when combinations are used.

While it is possible to carry out the reaction without the use of a catalyst, it is often preferable in order to assure a complete reaction, to utilize one or more catalysts as listed in amounts ranging from 0.001 to 1% based on the weight of the reactants. It is similarly advantagous to carry out the urethane synthesis at elevated temperature, usually between room temperature and 120° C. and preferable at 60° to 80° C. to obtain a complete reaction between 0.5 to 8 hours reaction time.

The reaction can be easily followed by titration of the isocyanate group or by infrared analysis.

The following examples 1 through 4 illustrate the synthesis and type of $R_f$-urethanes, thiourethanes and ureas belonging to Group A, derived from mono-, di- and triisocyanates and $R_f$-alcohols, mercaptans and amines.

EXAMPLE 1

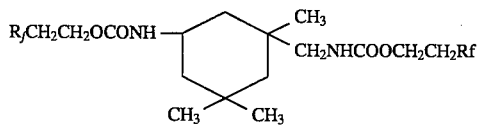

Isophorone diisocyanate (4.44 g, 0.02 moles) and $R_fCH_2CH_2OH$, wherein $R_f$ is $C_nF_{2n+1}$ and n is an even number from 6 to 14 and the average molecular weight is 516 (20.6 g, 0.04 moles) and stannous octoate (0.05 g) were mixed under nitrogen and heated with stirring to 90° C. for 2 hours. An infrared spectrum showed no —NCO absorption, indicating completion of the reaction. The product is a soft white wax, melting at 50°–56° C. NMR showed proton resonances at 4.8 ppm (1 proton NH), 4.5 ppm (1 proton NH), 4.4 ppm (4 protons CH$_2$OCO), 3.8–3.0 ppm (complex, 3 protons CH$_2$NH, CHNH), 2.5 ppm (4 protons R$_f$CH$_2$) and 2.0–0.8 ppm (complex, 15 protons, aliphatic ring and methyl protons).

EXAMPLE 2

1,12-diisocyanatododecane (5 g, 0.02 moles) and $R_fCH_2CH_2OH$ wherein $R_f$ is $C_nF_{2n+1}$, and n is an even number from 6 to 14 and the average molecular weight of the alcohol is 516 (20.6 g, 0.04 moles) were mixed under nitrogen and stirred at 125° C. for 8 hours. An infrared spectrum showed no —NCO absorption, indicating completion of the reaction. The product is a hard white wax melting at 118°–122° C. NMR showed proton resonances at 4.7 ppm (2 protons NH), 4.4 ppm (4 protons CH$_2$OCO), 3.2 ppm (4 protons CH$_2$CH$_2$NH), 2.5 ppm (4 protons R$_f$CH$_2$) and 1.3 ppm (20 protons NCH$_2$(CH$_2$)$_{10}$CH$_2$N).

EXAMPLE 3

Isophorone diisocyanate trimer (7.3 g, 0.01 moles), 2-pentanone (18.0 g), $C_6F_{13}CH_2CH_2OH$ (10.9 g, 0.03 moles) and dibutyl-tin dilaurate (0.02 g) were mixed under nitrogen and heated with stirring at 110° C. for 4 hours. An infrared spectrum showed no —NCO absorption, indicating completion of the reaction. The solvent was evaporated to yield a hard, white, waxy, solid melting at 128°–144° C. An infrared spectrum (KBr pellet) showed absorptions at 3320 cm$^{-1}$ (NH), 2960 cm$^{-1}$ (aliphatic CH), 1680 cm$^{-1}$ (C=O) and 1280 cm$^{-1}$ (CF).

EXAMPLE 4

DDI, a dimer acid derived diisocyanate, (6 g, 0.01 moles) and the $R_f$-alcohol used in Example 2 (10.32 g, 0.02 moles) were mixed under nitrogen and heated with stirring to 100° C. for 8 hours. An infrared spectrum showed no —NCO absorption, indicating completion of the reaction. The product is a tacky, yellow wax melting at 36°–45° C. NMR showed proton resonances at 4.7 ppm (2 protons NH), 4.4 ppm (4 protons CH$_2$OCO), 3.2 PPM (4 protons CH$_2$CH$_2$NH), 2.5 ppm (4 protons R$_f$CH$_2$), 1.6–0.8 ppm (72 protons, aliphatic dimer moiety).

The following examples 5 through 9 illustrate the synthesis and type of $R_f$-urethanes, thiourethanes and ureas belonging to Group B which are derived from mono-, di- and triisocyanates, $R_f$-alcohols, -mercaptans and -amines and in addition, nonfluorinated alcohols, mercaptans and amines with 1 to 36 carbon atoms.

EXAMPLE 5

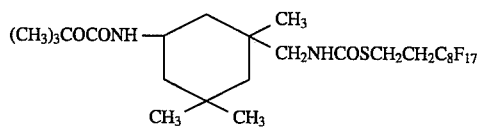

Isophorone diisocyanate (4.44 g, 0.02 moles), $C_8F_{17}CH_2CH_2SH$ (9.60 g, 0.02 moles) and 2.2.2 diazabicyclooctane (0.05 g) were mixed under nitrogen and heated with stirring to 90° C. for 2 hours. Isocyanate titration indicated completion of reaction and tertiary butyl alcohol (1.48 g, 0.02 moles) and dibutyltin dilaurate (0.05 g) were added. The reaction mixture was stirred at 90° C. for 4 hours and an infrared spectrum indicated complete reaction of the isocyanate groups. The product, obtained as a white wax, showed infrared absorptions at 3320 cm$^{-1}$ (NH), 2960 cm$^{-1}$ (aliphatic CH), 1680 cm$^{-1}$ (C=O) and 1280 cm$^{-1}$ (CF) and has a melting point of 22°–28° C.

EXAMPLE 6

Isophorone diisocyanate trimer (7.3 g, 0.01 moles), 2-pentanone (15 g) and sec-butyl amine (0.73 g, 0.01 moles) were stirred under nitrogen at room temperature for 1 hour. Isocyanate titration showed that all the amine had been consumed and $C_6F_{13}CH_2CH_2SH$ (7.6 g, 0.02 moles) and 2.2.2 diazabicyclooctane (0.02 g) were added to the reaction mixture. The temperature was raised to 90° C. and stirring was continued for 3 hours. The solvent was evaporated under reduced pressure to yield a yellow, glassy solid melting at 81°–93° C. An infrared spectrum (KBr pellet) showed absorptions at 3320 cm$^{-1}$ (NH), 2960 cm$^{-1}$ (aliphatic CH), 1680 cm$^{-1}$ (C=O) and 1280 cm$^{-1}$ (CF).

EXAMPLE 7

$C_{18}H_{37}NHCOOCH_2CH_2C_8F_{17}$

Octadecyl isocyanate (29.5 g, 0.1 moles) and $C_8F_{17}CH_2CH_2OH$ (46.4 g, 0.1 moles) were mixed under nitrogen and heated with stirring to 90° C. for 8 hours. An infrared spectrum showed no —NCO absorption, indicating completion of the reaction. The product is a white wax melting at 72°–75° C. NMR showed proton resonances at 4.7 ppm (1 proton NH), 4.4 ppm (2 proton $\underline{CH_2}OCO$—), 3.2 ppm (2 protons $CH_2\underline{CH_2}NH$), 2.5 ppm (2 protons $C_8F_{17}\underline{CH_2}$), 1.3 pm (32 protons $CH_3(\underline{CH_2})_{16}$) and 0.8 ppm (3 protons $\underline{CH_3}(CH_2)_{16}$).

EXAMPLE 8

$C_{18}H_{37}NHCOSCH_2CH_2C_8F_{17}$

Octadecyl isocyanate (29.5 g, 0.1 mole), $C_8F_{17}CH_2CH_2SH$ (48 g, 0.1 moles) and 2.2.2 diazabicyclooctane (0.1 g) were mixed under nitrogen and heated to 100° C. with stirring for 6 hours. An infrared spectrum showed no —NCO absorption, indicating completion of the reaction. The product is a white wax, melting at 85°–89° C. NMR showed proton resonances at 4.7 ppm (1 proton NH), 3.2 ppm (2 protons $CH_2\underline{CH_2}NH$), 3.1 ppm (2 protons $\underline{CH_2}SCO$), 2.5 ppm (2 protons $C_8F_{17}\underline{CH_2}$), 1.3 ppm (32 protons $CH_3(\underline{CH_2})_{16}$) and 0.8 ppm (3 protons $\underline{CH_3}(CH_2)_{16}$).

EXAMPLES 9 TO 16

Lubricants of this invention were evaluated either as ski waxes per se or blended with a commercial hydrocarbon ski wax, which was also serving as a standard for comparison.

The ski waxes were applied to the ski bases, using a standard hot melt application method, followed by scraping and buffing. The only wax applied differently was Toko TF 90 Paste Wax, also used as a standard for comparison, which was applied according to intructions given by the manufacturer. The TF 90 Paste Wax is a hydrocarbon wax containing Teflon powder as an additive.

The snow, weather and testing conditions on the test day were as follows:

| Weather: | Sunny, 8 °C. |
|---|---|
| Snow Temperature: | 1° C. |
| Snow Condition: | Wet, granular, machine groomed. |
| Test Course: | Straight, 200 m, 24° average angle. |

The top speed and total run time was measured and the average of three runs reported. Initial speed of runs was zero.

TABLE 1

| EXAMPLE | SKI WAX TESTED | TOP SPEED, km/hr | RUN TIME, SEC. |
|---|---|---|---|
| 9 | Toko Work Shop Wax | 86.0 | 18.3 |
| 10 | Toko TF 90 Paste | 87.5 | 17.9 |

TABLE 1-continued

| EXAMPLE | SKI WAX TESTED | TOP SPEED, km/hr | RUN TIME, SEC. |
|---|---|---|---|
|  | Wax |  |  |
| 11 | Wax of Example 1, applied over Toko Work Shop Wax | 87.5 | 17.7 |
| 12 | Wax Blend of 80% of Example 9, 5% of Example 1 and 15% of Example 7. | 88.5 | 17.6 |
| 13 | Wax Blend of 80% of Example 9, 5% of Example 4 and 15% of Example 8. | 89.0 | 17.3 |
| 14 | Wax Blend of 80% of Example 9 and 20% of Example 7. | 87.5 | 17.2 |
| 15 | Wax Blend of 50% of Example 9 and 50% of Example 7 | 90.0 | 16.9 |
| 16 | Wax Blend of 80% of Example 9 and 20% of Example 8. | 90.5 | 16.8 |

Examples 9 to 16 in Table 1 give the composition of the ski waxes and ski wax blends tested, including results obtained with two commercial ski waxes. The best total time achieved with a commercial ski wax, Toko TF-90 Paste Wax was 17.9 seconds, while average times achieved with the lubricants of this invention, used alone and in combination with a commercial hydrocarbon ski wax, ranged from 16.8 to 17.7 seconds.

What is claimed is:

1. Method for lubricating surfaces by applying a lubricant to said surfaces, said lubricant comprising compounds having the formula:

$[R_f—CH_2CH_2—X—CONH\}_m A\{NHCO—X—R_1]_n$ in which $R_f$ is a straight or branched perfluoroalkyl group of from 6 to 20 carbon atoms;

X is —O— or —S—;

$R_1$ is alkyl of from 8 to 36 carbon atoms;

m has a value of 1, 2, or 3;

n has a value of 0, 1, or 2;

the sum of m and n being 1, 2, or 3; and

A is $R_1$ if the sum of m and n is 1, and otherwise an aliphatic, cycloaliphatic, or aromatic group of up to 36 carbon atoms and having a valence equal to the sum of m and n.

2. The method of claim 1, wherein said surfaces are polymers of polyhydrocarbon type which can absorb said lubricant.

3. The method of claim 1, wherein said surfaces are surfaces which come in contact with ice, snow, or water.

4. The method of claim 1, said lubricant further comprising one or more organic and inorganic additives selected from the group consisting of powdered polyethylene, polytetrafluoroethylene, graphite, fluorinated graphite, and metal alloys.

5. The method of claim 1, wherein, $R_1$ is alkyl of from 12 to 36 carbon atoms.

6. The method of claim 5, wherein, $R_f$ is $C_nF_{2n+1}$ in which n is an even number of from 6 to 14.

7. The method of claim 1, wherein, m=1; n=0; A=$R_1$; and $R^1$ is a straight or branched alkyl of 12 to 36 carbon atoms.

8. The method of claim 7, wherein, $R_f$ is a straight or branched perfluoroalkyl group of from 6 to 14 carbon atoms.

9. The method of claim 8 wherein, X is —O—, and $R_1$ is octadecyl.

10. The method of claim 8 wherein, X is —S—, and $R_1$ is octadecyl.

11. The method of claim 1, wherein m=1; n=1; $R_1$ is alkyl of from 8 to 36 carbon atoms; and A is a divalent aliphatic or cycloaliphatic group of up to 36 carbon atoms.

12. The method of claim 11 wherein, $R_1$ is alkyl of from 12 to 36 carbon atoms.

13. The method of claim 12 wherein, $R_f$ is $C_nF_{2n+1}$ in which n is an even number of from 6 to 14.

14. The method of claim 1 wherein, m=2; n=0;

each $R_f$, independently of each other, is a straight or branched perfluoroalkyl group of from 6 to 20 carbon atoms;

each X, independently of each other, is —O— or —S—; and

A is a divalent aliphatic or cycloaliphatic group of up to 36 carbon atoms.

15. The method of claim 14 wherein, each $R_f$ is $C_nF_{2n+1}$ in which n is an even number of from 6 to 14.

16. The method of claim 15 wherein, each X is —O— and A is —$(CH_2)_{12}$—.

17. The method of claim 1 wherein, the sum of n and m is 3.

18. The method of claim 17 wherein, $R_1$ is alkyl of from 12 to 36 carbon atoms.

19. The method of claim 18 wherein, $R_f$ is $C_nF_{2n+1}$ in which n is an even number of from 6 to 14.

20. The method of claim 7 wherein, X is O; $R_f$ is a straight or branched perfluoroalkyl group of from 8 to 16 carbon atoms; and A is an alkyl group of from 12 to 18 carbon atoms.

21. The method of claim 1 wherein, the sum of m and n is 2 or 3 and A is an aliphatic, cycloaliphatic, or aromatic group of 18 to 36 carbon atoms and having a valence equal to the sum of m and n.

22. The method of claim 1, wherein, said lubricant has a melting point ranging from about 50° C. to about 110° C.

23. The method of claim 1 wherein, said lubricant further comprises one or more hydrocarbon waxes.

24. The method of claim 1 wherein, said lubricant further comprises one or more perfluoroalkanes.

25. The method of claim 3 wherein, said surfaces which come in contact with ice, snow, or water are snow skis, water skis, snow boards, sleds, snow mobiles, slipaways, surfboards, body boards, boogie boards, jet skis, or boats.

* * * * *